(12) United States Patent
Moriya et al.

(10) Patent No.: US 7,470,235 B2
(45) Date of Patent: Dec. 30, 2008

(54) PULSE WAVE DETECTING DEVICE AND METHOD THEREFOR

(75) Inventors: Akihisa Moriya, Kanagawa (JP); Takuji Suzuki, Kanagawa (JP); Kazushige Ouchi, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 519 days.

(21) Appl. No.: 11/233,022

(22) Filed: Sep. 23, 2005

(65) Prior Publication Data
US 2006/0224054 A1  Oct. 5, 2006

(30) Foreign Application Priority Data
Mar. 30, 2005  (JP)  ............... 2005-100131

(51) Int. Cl.
*A61B 5/02* (2006.01)
(52) U.S. Cl. .................................. 600/500
(58) Field of Classification Search ............. 600/485, 600/500–503
See application file for complete search history.

(56) References Cited

U.S. PATENT DOCUMENTS 5,285,783 A * 2/1994 Secker ................ 600/323
6,491,647 B1 * 12/2002 Bridger et al. ............. 600/585
6,811,535 B2 * 11/2004 Palti et al. .................. 600/499
2003/0181795 A1  9/2003 Suzuki et al.

FOREIGN PATENT DOCUMENTS

JP  2000-107147  4/2000
JP  2002-360530  12/2002

OTHER PUBLICATIONS

U.S. Appl. No. 11/233,022, filed Sep. 23, 2005, Moriya et al.
U.S. Appl. No. 11/326,511, filed Jan. 6, 2006, Moriya et al.
U.S. Appl. No. 11/233,022, filed Sep. 23, 2005, Moriya et al.
U.S. Appl. No. 11/345,292, filed Feb. 2, 2006, Suzuki et al.
U.S. Appl. No. 11/233,022, filed Sep. 23, 2005, Moriya et al.
U.S. Appl. No. 11/232,988, filed Sep. 23, 2005, Suzuki et al.

* cited by examiner

*Primary Examiner*—Charles A Marmor, II
*Assistant Examiner*—Christian Y. Jang
(74) *Attorney, Agent, or Firm*—Oblon, Spivak, McClelland, Maier & Neustadt, P.C.

(57) ABSTRACT

A pulse wave measuring apparatus can determine an optimum combination of a pair of light-emitting element and light-receiving element out of plural light-emitting elements and plural light-receiving elements on a real time basis according to a difference of signal intensity of a pulse wave signal from the light-receiving element and always measure an stable pulse wave of a wrist artery robustly.

7 Claims, 10 Drawing Sheets

PULSE WAVE DETECTING DEVICE AND METHOD THEREFOR

CROSS-REFERENCE TO RELATED APPLICATIONS

This application is based upon and claims the benefit of priority from the prior Japanese Patent Application No. 2005-100131, filed on 30 Mar. 2005, the entire contents of which are incorporated herein by reference.

TECHNICAL FIELD

The invention relates to a pulse wave measuring apparatus and a method therefor that are used for the purpose of autonomous nervous system measurement, sleep state measurement, health care, and the like.

BACKGROUND OF THE INVENTION

Heart beats representing various states of a human are used as useful indicators in various fields such as health care, sleep state measurement, and medical treatment. There are mainly two methods for measuring heartbeats. One is a method using an electrocardiogram obtained from an electrode between two points flanking the heart and a reference electrode. The other is a method of capturing pulse waves due to blood flows through blood capillaries or the like synchronizing with the heartbeats.

It is difficult for ordinary healthy people to use the method using an electrocardiogram in their daily lives.

The pulse wave measuring method mainly includes a reflection type method and a transmission type method. Both the reflection type method and the transmission type method use a difference of light absorbing characteristics of intravascular substances. In the reflection type method, light-emitting elements and light-receiving elements are arranged side by side on a surface of an organism. Light is irradiated on peripheral blood vessels and an amount of reflected light is captured by the light-receiving elements (see, for example, JP-A-2000-107147 and JP-A-2002-360530). In the transmission type method, light-emitting elements and light-receiving elements are arranged to sandwich an organism to capture an amount of light transmitted through a blood vessel with the light-receiving elements.

Pulse waves are measured for various purposes such as autonomous nervous system measurement, prevention of life-style related diseases, and sleep state measurement. There is an advantage that pulse waves can be measured easily. However, since a measurement site is a fingertip, an earlobe, a wrist, or the like, the measurement of pulse waves is strongly affected by movement and is susceptible to disturbances such as movement in daily lives.

Therefore, the invention provides a pulse wave measuring apparatus and a method therefor that copes with a positional deviation of a sensor module and a change in a position of an artery on a real time basis and is robust against disturbances.

BRIEF SUMMARY OF THE INVENTION

According to an embodiment of the invention, there is provided a measuring apparatus for detecting a pulse wave signal indicating a change in a blood flow in the blood vessel of a patient by using light, comprising: a sensor module including a plurality of light-emitting elements to irradiate the blood vessel, and a plurality of light-receiving elements to receive reflected light as a pulse wave signal from the blood vessel, each element being attached on the surface of the patient; a processor for light emission that causes the plural light-emitting elements to emit light one after another; an autocorrelation value calculating processor that calculates autocorrelation values of respective pulse wave signals corresponding to respective combinations of the light-emitting elements, which have emitted light, and the light-receiving elements, which have received light, respectively; and an optimum position identifying processor that selects a combination of a light-emitting element and a light-receiving element, which has outputted a pulse wave signal with a highest autocorrelation value among the respective autocorrelation values, as an optimum combination.

According to the embodiment of the invention, it is possible to select a combination of the plural light-receiving elements and the plural light-emitting elements, which are arranged on the surface of the organism of the subject, on a real time basis and always measure stable robust pulse waves.

DETAILED DESCRIPTION OF THE INVENTION

Embodiments of the invention will be explained with reference to the accompanying drawings.

FIRST EMBODIMENT

A pulse wave measuring apparatus 10 in a first embodiment of the invention will be hereinafter explained with reference to FIGS. 1 to 7.

(1) Structure of the Pulse Wave Measuring Apparatus 10

Figure 1:
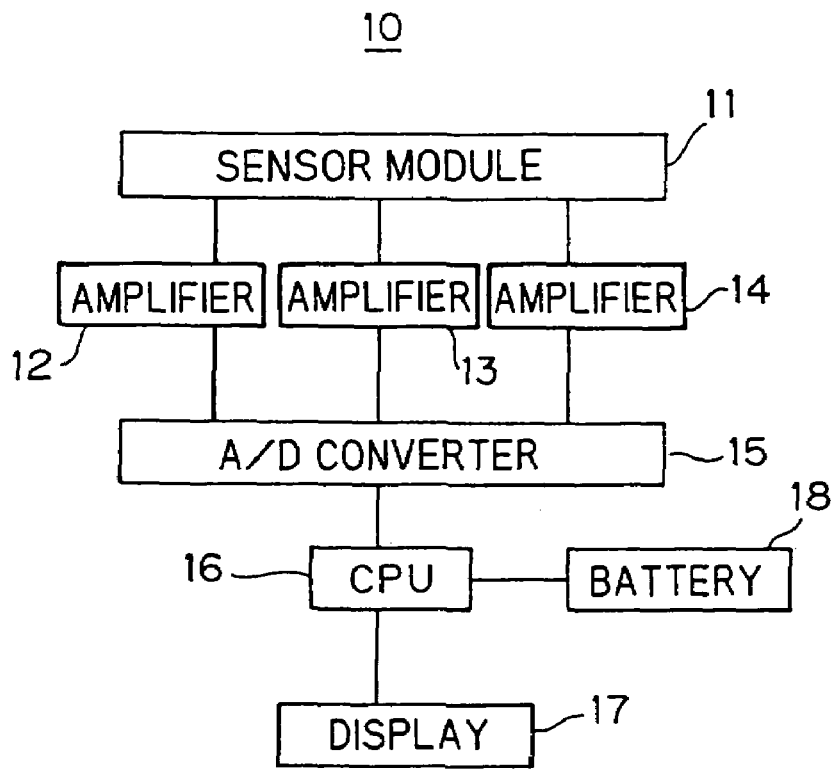
FIG. 1 is a block diagram of a pulse wave measuring apparatus according to a first embodiment of the invention.
Figure 2:
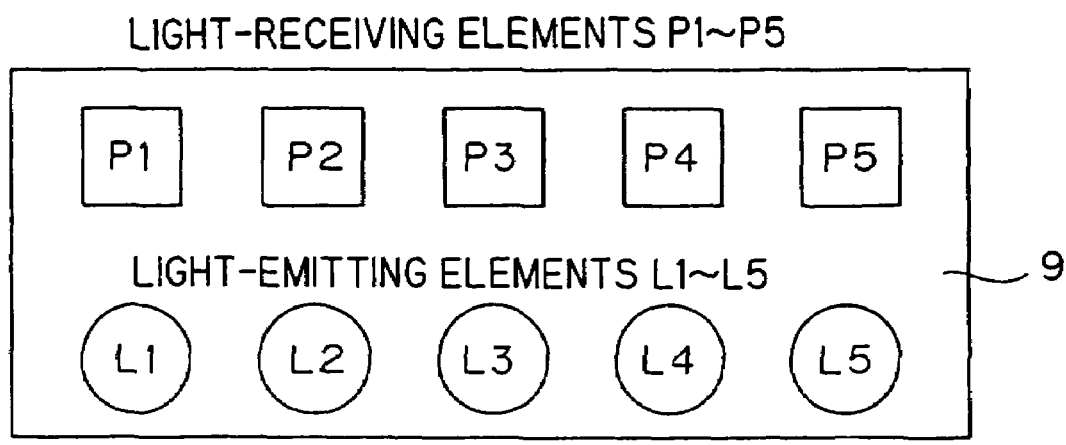
FIG. 2 is a diagram of a first example of arrangement of light-emitting elements and light-receiving elements in a sensor module of the pulse wave measuring apparatus.
Figure 3:
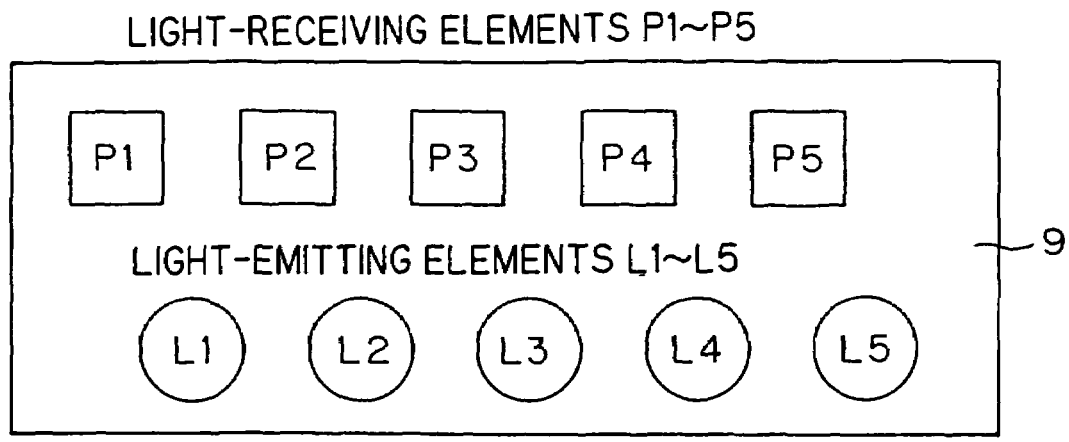
FIG. 3 is a diagram of a second example of the arrangement of light-emitting elements and light-receiving elements in the sensor module of the pulse wave measuring apparatus.
Figure 4:
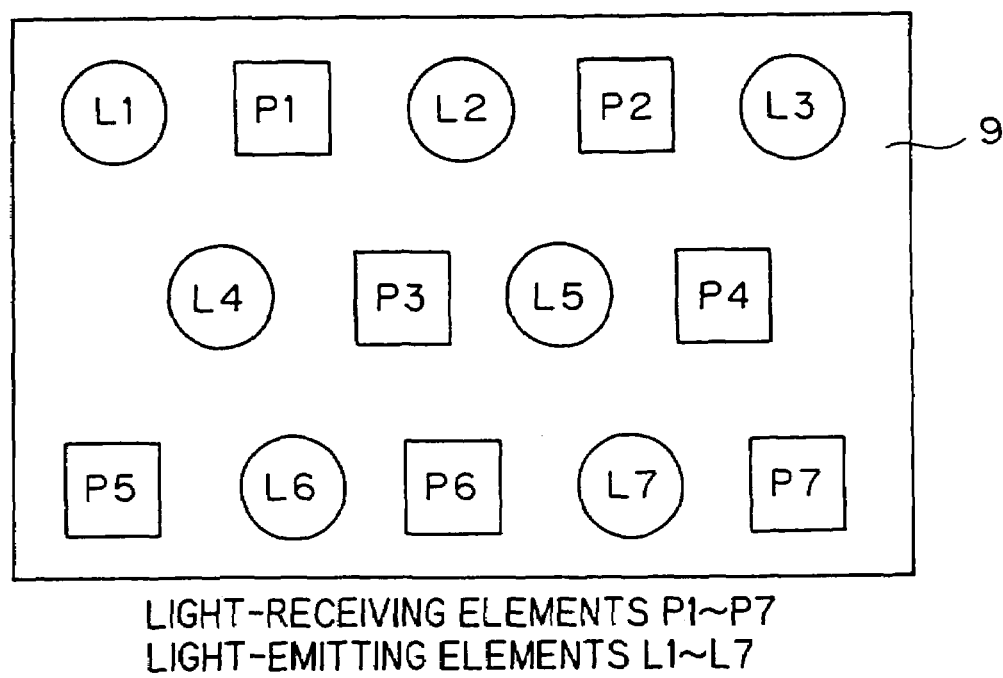
FIG. 4 is a diagram of a third example of the arrangement of light-emitting elements and light-receiving elements in the sensor module of the pulse wave measuring apparatus.

FIG. 1 is a block diagram showing a structure of the pulse wave measuring apparatus 10. FIGS. 2, 3, and 4 are diagrams showing example of arrangement of plural light-emitting elements L and plural light-receiving elements P in a sensor module 11. As shown in FIG. 1, the pulse wave measuring apparatus 10 amplifies a pulse wave signal, which is obtained from the sensor module 11, with amplifiers 12 to 14 and, then, converts the pulse wave signal into a digital signal with an A/D converter 15. Thereafter, the pulse wave measuring apparatus 10 processes the digital signal with a CPU 15 and displays a result of the processing on a display 17. Electric power for the pulse wave measuring device 10 is supplied from a battery 18. Infrared LEDs are used for the light-emitting elements L of the sensor module 11 and photodiodes are used for the light-receiving elements P. Note that a program for realizing a processing method for measurement of a pulse wave described below is stored in the pulse wave measuring device 10 and is processed by the CPU 15.

A structure of the sensor module 11 will be explained. The plural light-emitting elements L and the plural light-receiving elements P are provided on an array substrate 9 of the sensor module 11. The light-emitting elements L and the light-receiving elements P are attached to a wrist or the like.

FIG. 2 is a diagram of a first example of arrangement of the light-emitting elements L and the light-receiving elements P on the array substrate 9. This is standard arrangement of the light-emitting elements L and the light-receiving elements P in the sensor module 11. Light-emitting elements L1 to L5 are arranged one after another in a row in the horizontal direction and light-receiving elements P1 to P5 are arranged one after another in a row in the horizontal direction in parallel to the light-emitting elements L1 to L5. The light-emitting element L1 and the light-receiving element P1 are in a one-to-one relation. The same holds true for the other light-emitting elements L2 to L5 and the other light-receiving elements P2 to P5. When the sensor module 11 is attached to a wrist 19, the plural light-emitting elements L and the plural light-receiving elements P are wound along the periphery of the wrist 19.

FIG. 3 is a diagram of a second example of the attachment, in which two light-emitting elements L are associated with one light-receiving element P. The light-emitting elements L1 to L5 are arranged one after another in a row in the horizontal direction and the light-receiving elements P1 to P5 are arranged one after another in a row in the horizontal direction such that the light-emitting elements L deviate in the horizontal direction with respect to the light-receiving elements P. With the arrangement shown in FIG. 3, the light emitting elements L and the light-receiving elements P are excellent in detection of a position when the sensor module 11 is attached.

FIG. 4 is a third example of the arrangement, in which the arrangement in FIG. 3 is further expanded. The light-emitting elements L and the light-receiving elements P are also arranged in the vertical direction to aim at further improvement of detection accuracy. The light-emitting elements L and the light-receiving elements P are arranged alternately in a row in the horizontal direction. The row in the horizontal direction, in which the light-emitting elements L and the light-receiving elements P are arranged in this way, are arranged in plural stages in the vertical direction.

(2) Processing Method of the Pulse Wave Measuring Apparatus 10

Figure 6:
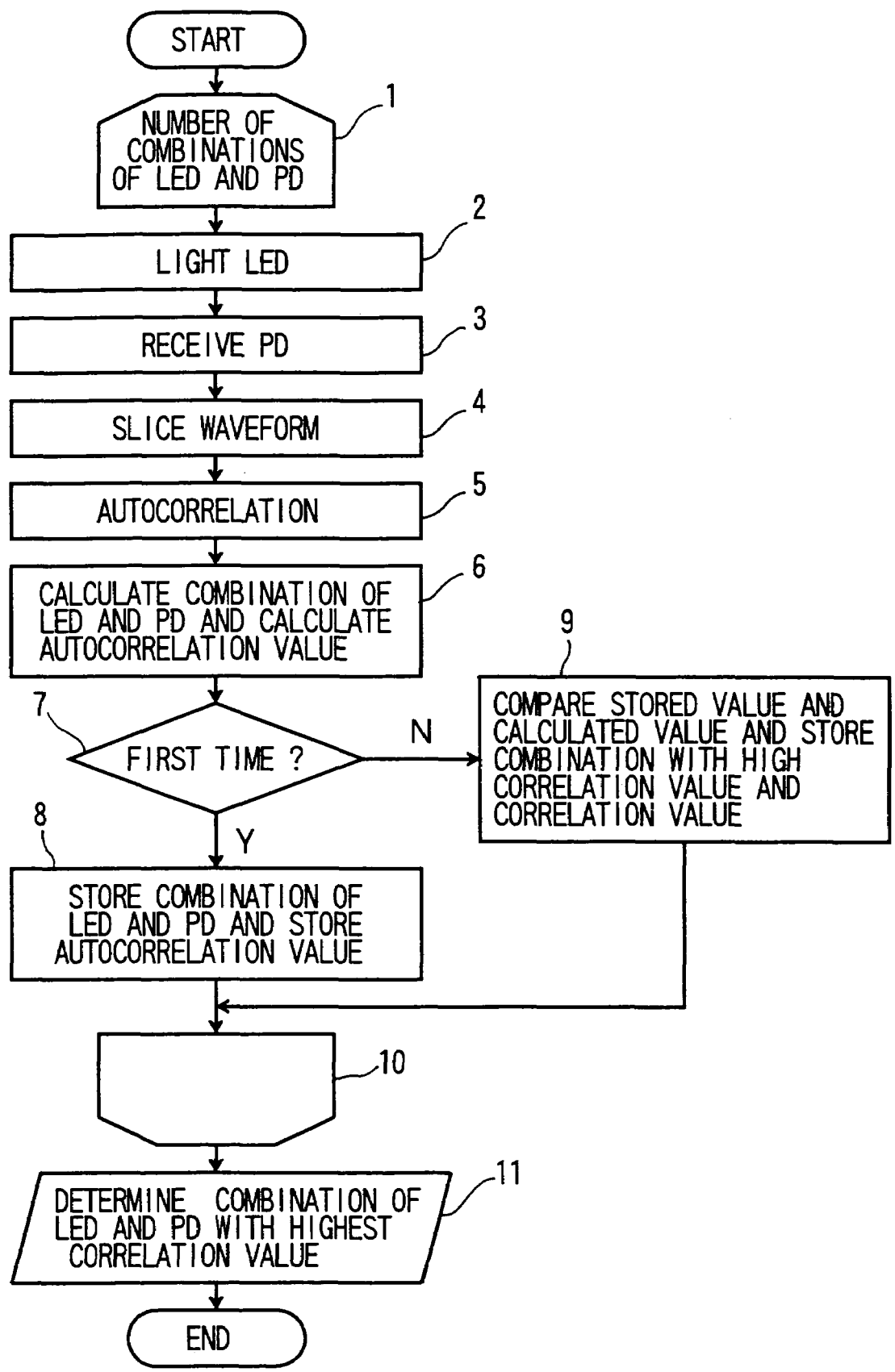
FIG. 6 is a flowchart of the pulse wave measuring apparatus.

A processing method of the pulse wave measuring apparatus 10 will be explained using the sensor module 11 shown in FIG. 2 with reference to a flowchart in FIG. 6.

Figure 5:
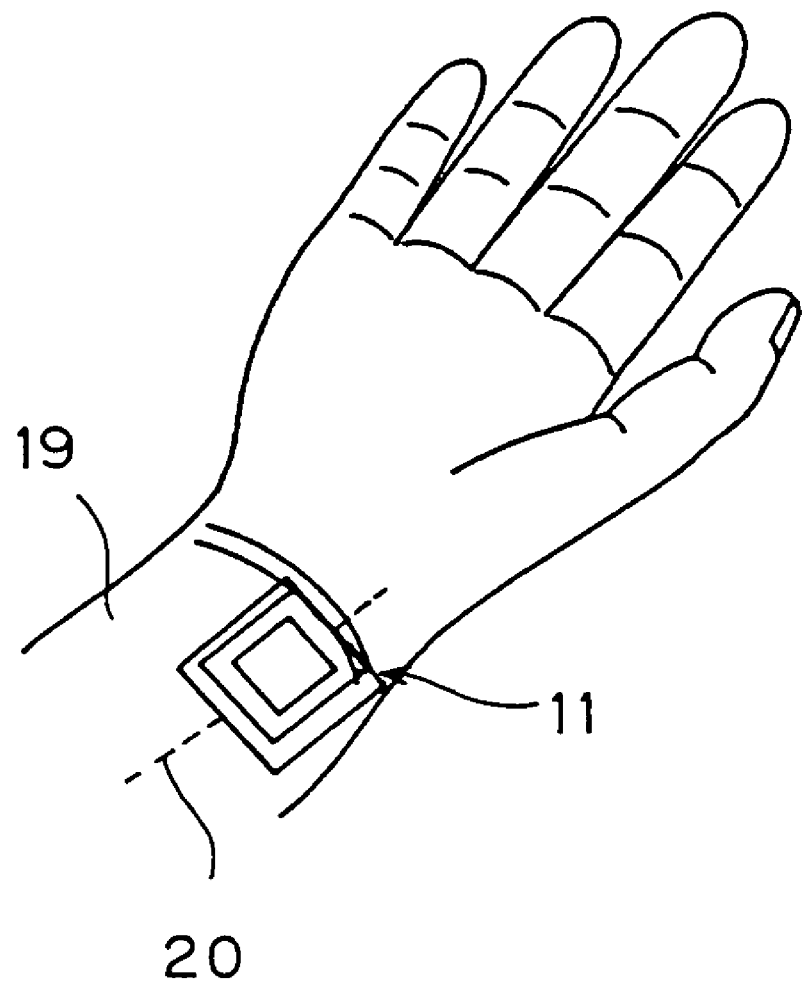
FIG. 5 is a perspective view showing an optimum attaching site of the pulse wave measuring apparatus.

First, the sensor module 11 is attached on an artery 20 in a wrist 19 of a patient as shown in FIG. 5.

In step 1, the pulse wave measuring apparatus 10 sets processing to be performed for all combinations of the light-emitting elements L and the light-receiving elements P.

In step 2, the pulse wave measuring apparatus 10 causes the light-emitting element L1 to emit light.

In step 3, the pulse wave measuring apparatus 10 receives reflection intensity of the light from the light-emitting element L1 in the light-receiving elements P1 to P5 and stores a pulse wave signal of a light-receiving element with strongest signal intensity. For example, the pulse wave signal is assumed to be a pulse wave signal Y(t) of the light-receiving element P3.

In step 4, the pulse wave measuring device 10 slices a pulse waveform for one heart beat that is obtained when the pulse wave signal Y(t) is measured for a fixed period. The fixed period is 1.0 to 1.5 seconds.

In step 5, the pulse wave measuring apparatus 10 compares a sliced pulse waveform H for one heart beat and the pulse wave signal Y(t), which is continuously inputted, to obtain an autocorrelation S(t). For example, the autocorrelation S(t) is equal to or higher than −1 and equal to or lower than 1. The autocorrelation S(t) is the highest at 1.

In step 6, the pulse wave measuring apparatus 10 calculates an autocorrelation value S0 that is a value obtained by averaging the autocorrelation S(t) in a predetermined time (e.g., five seconds). If a value of the autocorrelation S(t) in a fixed time is constant, the autocorrelation value S0 is high (e.g., S0>0.8). A signal intensity of a pulse wave signal from the light-receiving element is stably high and it can be judged that the pulse wave signal is a pulse wave. If the signal intensity is unstable, it can be judged that the pulse wave signal is noise.

In step 7, the calculated autocorrelation value S0 is an autocorrelation value measured for the first time, the pulse wave measuring apparatus 10 proceeds to step 8. If the calculated autocorrelation value S0 is the autocorrelation value S0 calculated for the second or subsequent time, the pulse wave measuring apparatus 10 proceeds to step 9. In other words, when combinations of the light-emitting element L1 and the light-receiving elements P1 to P5 are processed first, the autocorrelation value S0 highest in the combinations is set as the autocorrelation value S0 at the first time.

In step 8, the pulse wave measuring apparatus 10 stores the calculated autocorrelation value S0 at the first time as an initial value.

In step 9, if the calculated autocorrelation value S0 is high compared with the initial value stored in step 8 in advance or the autocorrelation value S0 updated in processing in step 9 of the last time, the pulse wave measuring apparatus 10 updates the initial value or the updated autocorrelation value S0 to the calculated autocorrelation value S0 and stores the calculated autocorrelation value S0. If the calculated autocorrelation value S0 is low compared with the initial value stored in step 8 in advance or the autocorrelation value S0 updated in processing in step 9 of the last time, the pulse wave measuring apparatus 10 does not update the initial value or the updated autocorrelation value S0.

In step S10, the pulse wave measuring apparatus 10 repeats the processing from step 1 until processing for all combinations of the light-emitting elements L and the light-receiving elements P ends. When the processing for all the combinations ends, the pulse wave measuring apparatus 10 proceeds to step 11.

Figure 7:
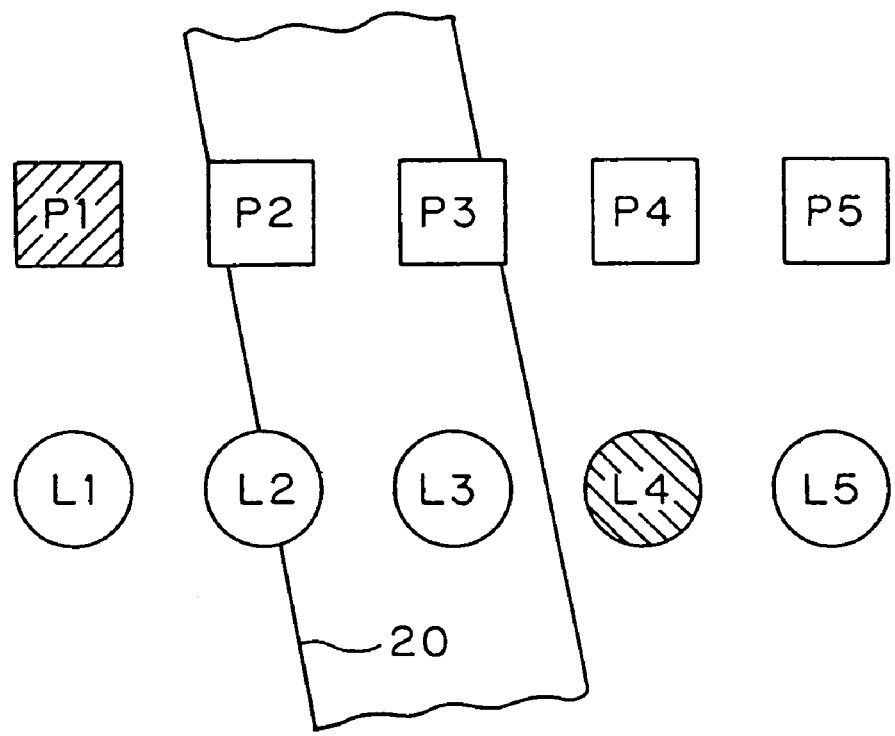
FIG. 7 is a diagram of an optimum combination of a light-emitting element and a light-receiving element in the pulse wave measuring apparatus.

In step 11, the pulse wave measuring apparatus 10 determines a combination of the light-emitting element L and the light-receiving element P having the highest autocorrelation value. For example, when it is assumed that the combination is a combination of the light-emitting element L4 and the light-receiving element P1, the combination is as shown in FIG. 7.

With the processing described above, although the pulse wave measuring apparatus 10 in this embodiment has the plural light-emitting elements L and the plural light-receiving elements P, the pulse wave measuring apparatus 10 can identify an optimum position. Thus, it is possible to realize the wave pulse measuring apparatus that copes with a positional deviation of the sensor module 11 and a change in a position of the artery 20 on a real time basis and is robust against disturbances.

SECOND EMBODIMENT

A second embodiment of the invention will be explained with reference to FIGS. 8 to 11.

In this embodiment, a method of selecting an optimum combination of the light-emitting element L and the light-receiving element P, which occurs when a position of the blood vessel (the artery) 20 changes in the pulse wave measuring device 10, will be explained.

Figure 8:
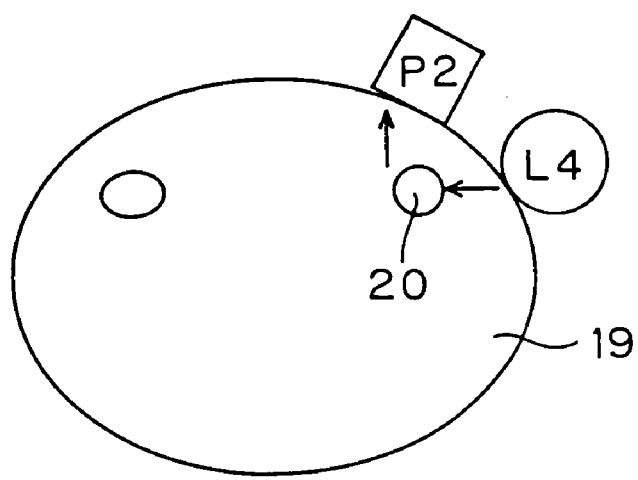
FIG. 8 is a sectional view showing positions of a sensor module and an artery before a change of an artery position in a second embodiment of the invention.
Figure 9:
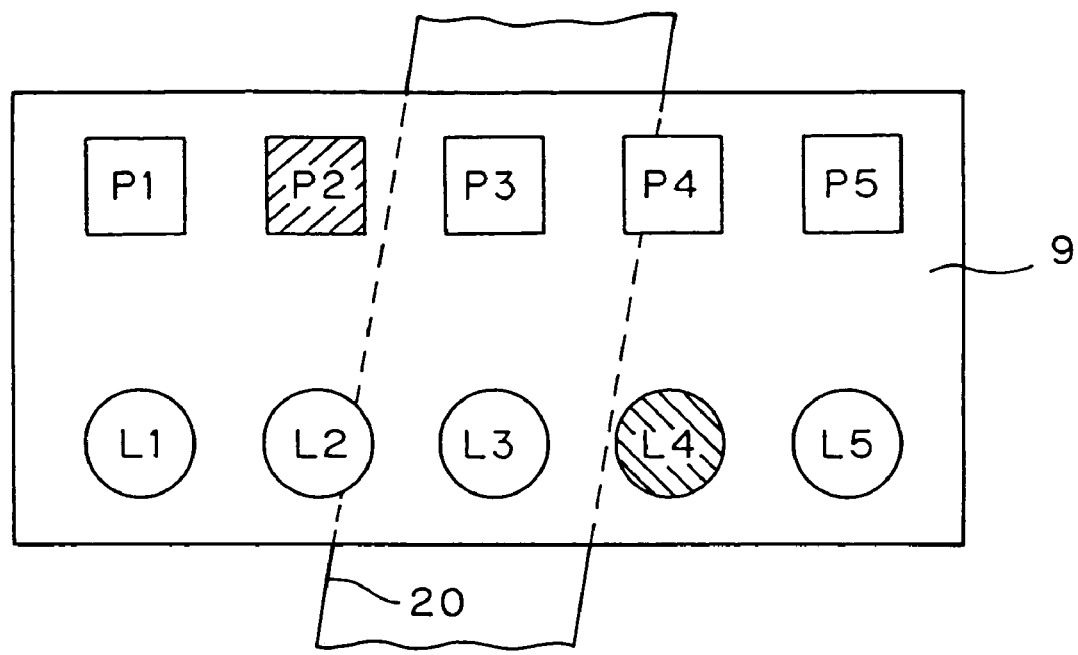
FIG. 9 is a diagram of the positions of the sensor module and the artery before the change of the artery position viewed from a surface of an organism in the second embodiment.
Figure 10:
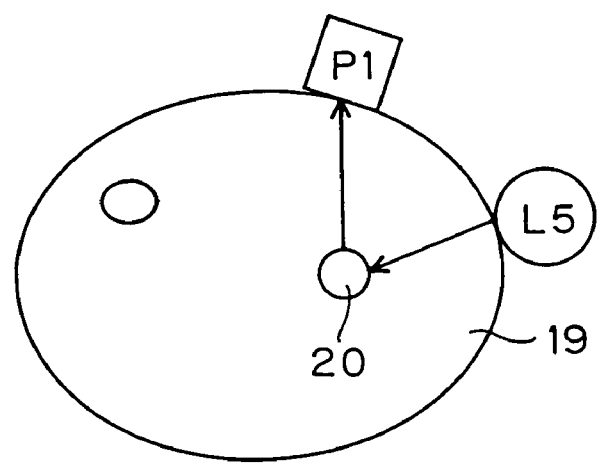
FIG. 10 is a sectional view showing positions of the sensor module and the artery after the change of the artery position in the second embodiment.
Figure 11:
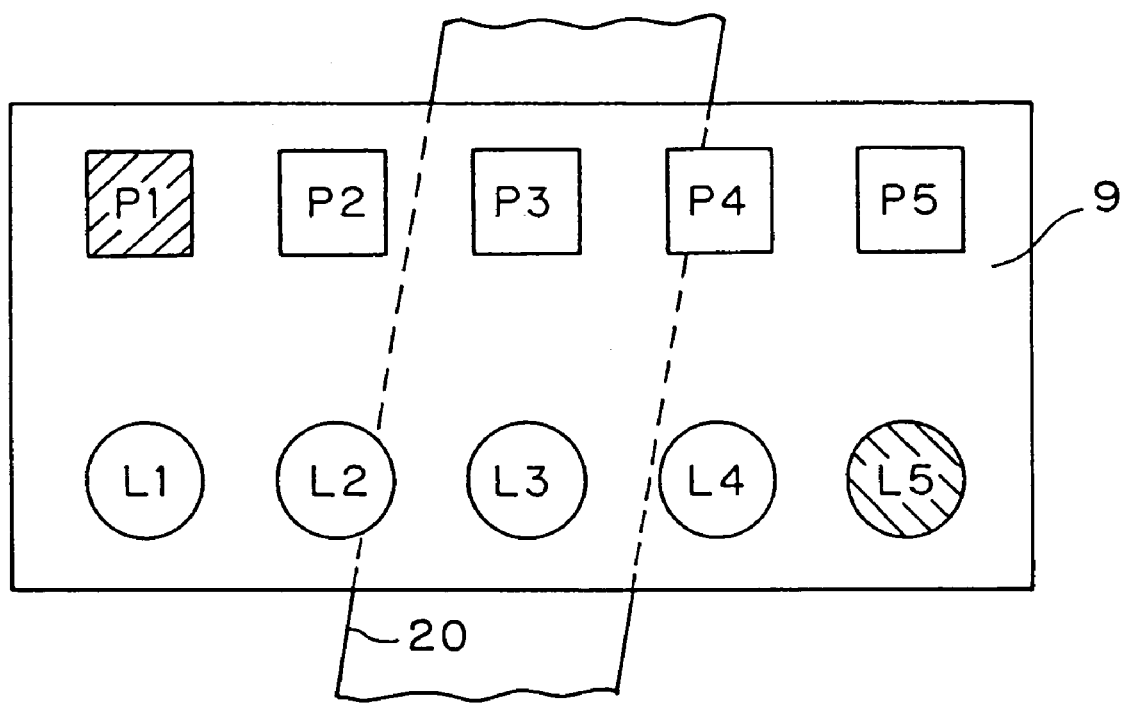
FIG. 11 is a diagram of the positions of the sensor module and the artery after the change of the artery position viewed from the surface of the organism in the second embodiment.

FIGS. 8 and 10 are sectional views showing positions of the sensor module 11 and the artery 20 of the wrist 19. FIGS. 9 and 11 are schematic diagrams of the sensor module 11 and the artery 20 viewed from a surface of an organism. In FIGS. 9 and 11, positions of the sensor module 11 and the artery 20 before and after a change of a position of the artery 20 are shown, respectively.

As a characteristic of the light-emitting elements L used in the sensor module 11 in this embodiment, when light is made incident in an organism and the light is reflected to return to the outside of the organism, a distance between the light-emitting elements L and the light-receiving elements P is proportional to a depth of the light made incident in the organism. As the distance of the light-emitting elements L and the light-receiving elements P are larger, the depth of the light made incident in the organism detected by the light-receiving elements P is larger.

In FIGS. 8 and 9, the artery 20 is close to the surface of the organism. Since the artery 20 is close to the surface of the organism, an interval between the light-emitting elements L and the light-receiving elements P is preferably small. A combination of the light-emitting element L4 and the light-receiving element P2 shown in FIG. 9 is appropriate.

In FIGS. 10 and 11, the artery 20 is far from the surface of the organism. Since the artery 20 is far from the surface of the organism, an interval between the light-emitting elements L and the light-receiving elements P is preferably large. A combination of the light-emitting element L5 and the light-receiving element P1 shown in FIG. 11 is appropriate.

THIRD EMBODIMENT

Figure 12:
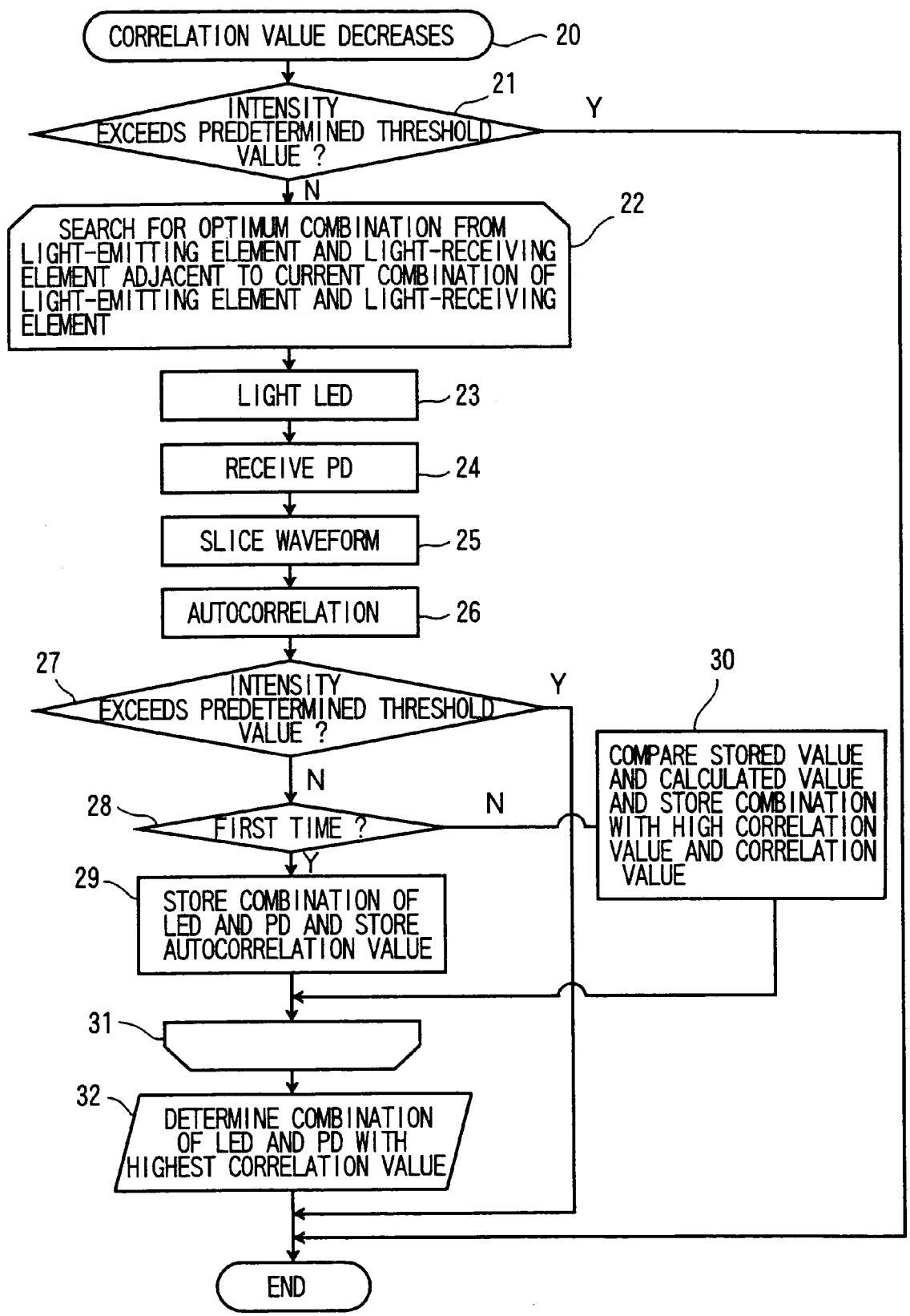
FIG. 12 is a flowchart of a pulse wave measuring apparatus according to a third embodiment of the invention.

A third embodiment of the invention will be explained with reference to FIG. 12.

In this embodiment, assuming that an optimum combination of a pair of the light-emitting element L and the light-receiving element P has already been acquired by the method explained in the first embodiment, a method of causing the light-emitting elements P to emit light selectively in selecting an optimum combination again will be explained.

When a currently selected combination of a pair of the light-emitting element L and the light-receiving element P is as shown in FIG. 2, if intensity of a pulse wave signal weakens in the combination because of influence of movement, the pulse wave measuring apparatus 10 tries to search for an optimum combination again.

In this search, the pulse wave measuring apparatus does not cause the light-emitting elements L to emit light in order from the light-emitting element L1. Instead, as indicated by steps 20 to 22 in a flowchart in FIG. 12, the pulse wave measuring apparatus 10 causes the light-emitting elements L to emit light in order from the light-emitting element L near the currently selected light-emitting element L. This makes it possible to select an optimum combination by performing light emission as a small number of times as possible. In that case, as indicated by step 21, if a pulse wave signal has intensity equal to or higher than a certain threshold value, which allows the pulse wave signal to be used as a pulse wave, the pulse wave measuring apparatus 10 stops the search for an optimum combination at that time. Note that steps 23 to 32 are the same as the processing in steps 2 to 11.

FOURTH EMBODIMENT

A fourth embodiment of the invention will be explained with reference to FIG. 13.

Apart from a combination of the light-emitting element L and the light-receiving element P with a high autocorrelation value calculated according to autocorrelation, intensity of a pulse wave signal may be equal to or lower than a predetermined threshold value.

Figure 13:
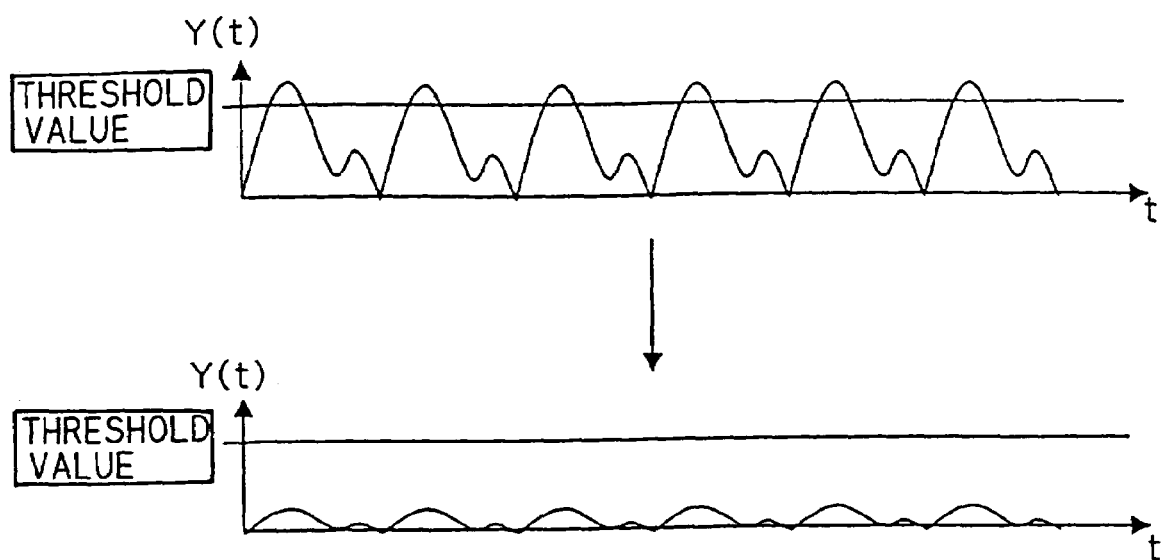
FIG. 13 is a diagram showing a difference of changes in a pulse wave amplitude in a fourth embodiment of the invention.

In this embodiment, as shown in FIG. 13, when an amplitude of the pulse wave signal Y(t) falls to be lower than the predetermined threshold value, the pulse wave measuring apparatus 10 detects a combination of the light-emitting element L and the light-receiving element P, which has the pulse wave signal Y(t) with signal intensity equal to or higher than the threshold value, again.

Consequently, it is possible to realize robust pulse wave measurement.

FIFTH EMBODIMENT

Figure 14:
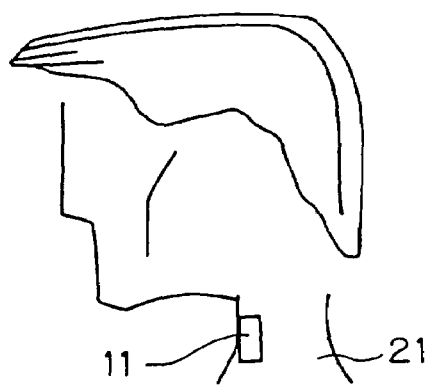
FIG. 14 is a diagram of an attaching position of a sensor module in a fifth embodiment of the invention.

A fifth embodiment of the invention will be explained with reference to FIG. 14.

In the first embodiment, the sensor module 11 is attached to a site near a radial artery or an ulnar artery of the wrist 19. However, in this embodiment, as shown in FIG. 14, the same effect as the first embodiment is obtained by attaching the sensor module 11 to a carotid artery of a neck 21.

SIXTH EMBODIMENT

A sixth embodiment of the invention will be explained with reference to FIGS. 15 and 16.

Figure 15:
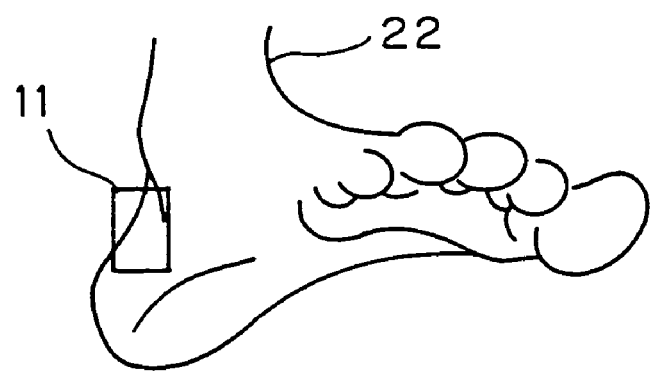
FIG. 15 is a diagram of an attaching position of a sensor module in a sixth embodiment of the invention.

In this embodiment, unlike the first and the sixth embodiments, the sensor module 11 is attached to a planta artery near an ankle 22 as shown in FIG. 15.

Figure 16:
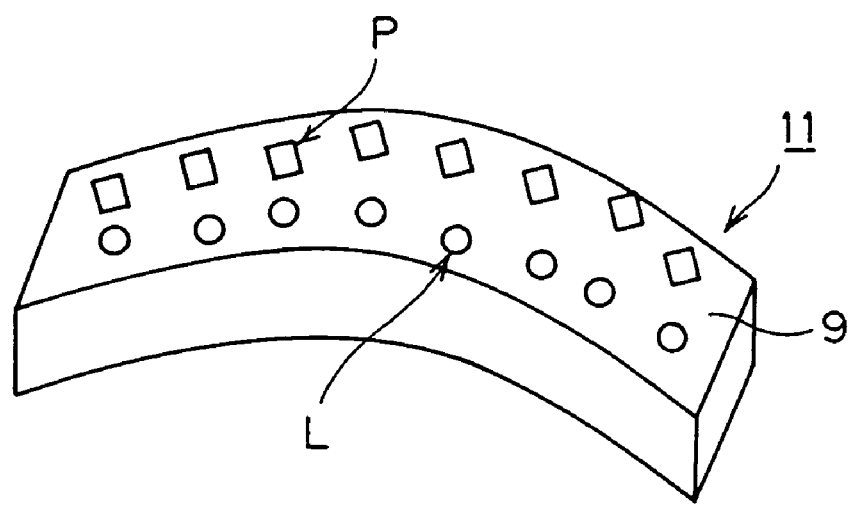
FIG. 16 is a diagram showing a shape of the sensor module in the sixth embodiment.

However, since a surface of the skin near the ankle 22 is extremely rough because of a melleolus, a pulse wave is detected by curving the sensor module 11 to stick firmly to the skin as shown in FIG. 16.

MODIFICATIONS

The invention is not limited to the embodiments described above and can be modified in various ways as long as modifications do not depart from the spirit of the invention.

The invention is suitably applied to measurement of a pulse wave for various purposes such as autonomous nervous system measurement, prevention of life-style related diseases, and sleep state measurement.

What is claimed is:

1. A measuring apparatus for detecting a pulse wave signal indicating a change in a blood flow in the blood vessel of a patient by using light, comprising:
   a sensor module including a plurality of light-emitting elements to irradiate the blood vessel, and a plurality of light-receiving elements to receive reflected light as a pulse wave signal from the blood vessel, each element being configured to be attached on the surface of the patient;
   a processor for light emission that causes the plurality of light-emitting elements to emit light one after another;
   an autocorrelation value calculating processor that calculates autocorrelation values of respective pulse wave signals corresponding to respective combinations of the light-emitting elements, which have emitted light, and the light-receiving elements, which have received light, respectively; and
   an optimum position identifying processor that selects a combination of a light-emitting element and a light-receiving element, which has outputted a pulse wave signal with a highest autocorrelation value among the respective autocorrelation values, as an optimum combination,
   wherein the autocorrelation value calculating processor slices waveforms of pulse wave signals in an arbitrary period from the pulse wave signals, respectively, and obtains an autocorrelation between the sliced waveforms and the pulse wave signals to thereby calculate autocorrelation values of the respective pulse wave signals.

2. A pulse wave measuring apparatus according to claim 1, wherein the arbitrary period includes a pulse wave of at least one beat.

3. A measuring apparatus for detecting a pulse wave signal indicating a change in a blood flow in the blood vessel of a patient by using light, comprising
   a sensor module including a plurality of light-emitting elements to irradiate the blood vessel, and a plurality of light-receiving elements to receive reflected light as a pulse wave signal from the blood vessel, each element being configured to be attached on a surface of the patient;
   a processor for light emission that causes the plurality of light-emitting elements to emit light one after another;
   an autocorrelation value calculating processor that calculates autocorrelation values of respective pulse wave signals corresponding to respective combinations of the lite-emitting elements, which have emitted light, and the light-receiving elements, which have received light, respectively; and
   an optimum position identifying processor that selects a combination for a light-emitting element and a light-receiving element, which has outputted a pulse wave signal with a highest autocorrelation value among the respective autocorrelation values, an optimum combination,
   wherein, in selecting an optimum combination again after an optimum combination of a light-emitting element and a light-receiving element is determined by the optimum position identifying processor, the processor for light emission causes a light-emitting element near the light-emitting element selected as the light-emitting of the optimum combination to emit light.

4. A measuring method of detecting a pulse wave signal indicating a change in a blood flow in a blood vessel of a patient by using light, comprising:
   causing a plurality of light-emitting elements provided in a sensor module to emit light one after another;
   calculating autocorrelation values of respective pulse wave signals corresponding to respective combinations of light-emitting elements that have emitted light, and light-receiving elements that have received light, respectively; and
   selecting a combination of a light-emitting element and a light-receiving element, which has outputted a pulse wave signal with a highest autocorrelation value among the respective autocorrelation values, as an optimum combination,
   wherein the step of calculating autocorrelation value includes slicing waveforms of pulse wave signals in an arbitrary period from the pulse wave signals, respectively, and obtaining an autocorrelation between the sliced waveforms and the pulse wave signals to thereby calculate autocorrelation values of the respective pulse wave signals.

5. A computer-readable medium encoded with a program that causes a computer to perform a measuring method of detecting a pulse wave signal indicating a change in a blood flow in the blood vessel of patient by using light, the program comprising the steps of:
   a light-emitting step of causing a plurality of light-emitting elements provided in a sensor module to emit light one after another;
   an input step of inputting respective pulse wave signals outputted from a plurality of light-receiving elements provided in the sensor module;
   an autocorrelation value calculating step of calculating autocorrelation values of respective pulse wave signals corresponding to respective combinations of light-emitting elements that have emitted light, and the light-receiving elements that have received light, respectively; and
   an optimum position identifying step of selecting a combination of a light-emitting element and a light-receiving element, which has outputted a pulse wave signal with a highest autocorrelation value among the respective autocorrelation values, as an optimum combination,
   wherein the autocorrelation value calculating step includes slicing waveforms of pulse wave signals in an arbitrary period from the pulse wave signals, respectively, and obtaining an autocorrelation between the sliced waveforms and the pulse wave signals to thereby calculate autocorrelation values of the respective pulse wave signals.

6. A measuring method of detecting a pulse wave signal indicating a change in a blood flow in the blood vessel of a patient by using light, comprising:
   causing a plurality of light-emitting elements provided in a sensor module to emit light one after another;

calculating autocorrelation values of respective pulse wave signals corresponding to respective combinations of the light-emitting elements, which have emitted light, and light-receiving elements, which have received light, respectively; and selecting a combination of a light-emitting element and a light-receiving element, which has outputted a pulse wave signal with a highest autocorrelation value among the respective autocorrelation values, as an optimum combination, wherein, in selecting an optimum combination again after an optimum combination of a light-emitting element and a light-receiving element is determined in the selecting step, a light-emitting element near the light-emitting element selected as the light-emitting of the optimum combination is caused to emit light.

7. A computer-related medium encoded with a program that causes a computer to perform a measuring method of detecting a pulse wave signal indicating a change in a blood flow in the blood vessel of patient by using light, the program comprising the steps of:

a light-emitting step of causing a plurality of light-emitting elements provided in a sensor module to emit light one after another;

an input step of inputting respective pulse wave signals outputted from light-receiving elements provided in the sensor module;

an autocorrelation value calculating step of calculating autocorrelation values of respective pulse wave signals corresponding to respective combinations of the light-emitting elements, which have emitted light, and the light-receiving elements, which have received light, respectively; and an optimum position identifying step of selecting a combination of a light-emitting element and a light-receiving element, which has outputted a pulse wave signal with a highest autocorrelation value among the respective autocorrelation values, as an optimum combination, wherein, in selecting an optimum combination again after an optimum combination of a light-emitting element and a light-receiving element is determined in the optimum position identifying step, a light-emitting element near the light-emitting element selected as the light-emitting of the optimum combination is caused to emit light.

* * * * *